United States Patent [19]

Hee

[11] Patent Number: 4,847,729

[45] Date of Patent: Jul. 11, 1989

[54] ELECTRICALLY CONDUCTIVE WRIST BRACELET WITH REMOVABLE CLASPING LINKS AND EXPANSION BAND

[75] Inventor: Roland Hee, Manila, Philippines

[73] Assignee: Jes, Inc., Newport Beach, Calif.

[21] Appl. No.: 237,493

[22] Filed: Aug. 26, 1988

Related U.S. Application Data

[63] Continuation of Ser. No. 39,633, Apr. 17, 1987, abandoned.

[51] Int. Cl.$^4$ ............................................. H05F 3/02
[52] U.S. Cl. .................................... 361/220; 224/175; 224/220
[58] Field of Search ............... 361/212, 220, 223, 224; 224/164, 165, 175, 219, 220, 267; 59/82; 439/37

[56] References Cited

U.S. PATENT DOCUMENTS

| | | | |
|---|---|---|---|
| 2,928,100 | 3/1960 | Gagnon | 57/82 X |
| 2,998,697 | 9/1961 | Augenstein | 59/82 X |
| 3,237,395 | 3/1966 | Bennett | 224/175 X |
| 3,377,509 | 7/1967 | Legge | 361/220 |
| 3,422,460 | 10/1966 | Burke | 57/901 X |
| 3,424,698 | 1/1969 | Lupinski | 252/500 |
| 3,459,997 | 8/1967 | Legge | 361/223 |
| 3,541,389 | 12/1968 | Van Name | 361/224 |
| 3,582,448 | 6/1971 | Okuhashi | 57/901 X |
| 3,596,134 | 7/1971 | Burke | 361/220 |
| 3,699,590 | 10/1972 | Webber | 57/901 X |
| 3,812,861 | 5/1974 | Peters | 361/220 X |
| 3,832,841 | 9/1974 | Cole | 57/207 |
| 3,851,456 | 12/1974 | Hamada | 57/901 X |
| 3,857,397 | 12/1974 | Brosseau | 361/220 X |
| 3,904,929 | 9/1975 | Kanaya | 361/220 |
| 3,986,530 | 10/1976 | Maekawa | 139/425 R |
| 3,987,613 | 10/1976 | Woods | 57/901 X |
| 4,267,233 | 5/1981 | Tanaka | 428/389 |
| 4,321,789 | 3/1982 | Dammann | 57/224 |
| 4,373,175 | 2/1983 | Mykkanen | 361/220 |
| 4,398,277 | 8/1983 | Christiansen | 361/220 |
| 4,402,560 | 9/1983 | Swainbank | 439/37 |
| 4,420,529 | 12/1983 | Westhead | 428/244 |
| 4,422,483 | 12/1983 | Zins | 139/420 |
| 4,459,633 | 7/1984 | Vandermark | 361/220 |
| 4,475,141 | 10/1984 | Antonevich | 361/220 |
| 4,577,256 | 3/1986 | Breidegam | 361/220 |
| 4,639,825 | 1/1987 | Breidegam | 361/212 |

FOREIGN PATENT DOCUMENTS 2547390 10/1975 Fed. Rep. of Germany .

Primary Examiner—L. T. Hix
Assistant Examiner—Brian W. Brown
Attorney, Agent, or Firm—Stetina and Brunda

[57] ABSTRACT

A spring-biased expansion band of metal bar members, attaches to a clasp member at one end and to a linear array of separately removeable and replaceable links at the other end to complete the bracelet. Each link has a pivot bar at one end and a complementary shaped aperture at the other end which engages the pivot bar upon an adjacent link. Size adjustment is obtained by user insertion or removal of one or more links from the band. The band and clasp member are electrically conductive at the bracelet's interior circumference, but electrically insulating at the bracelet's exterior circumference. A grounding cord connects to the conductive surface through a swivel and snap electrical connector at the clasp member.

18 Claims, 1 Drawing Sheet

U.S. Patent    Jul. 11, 1989    4,847,729
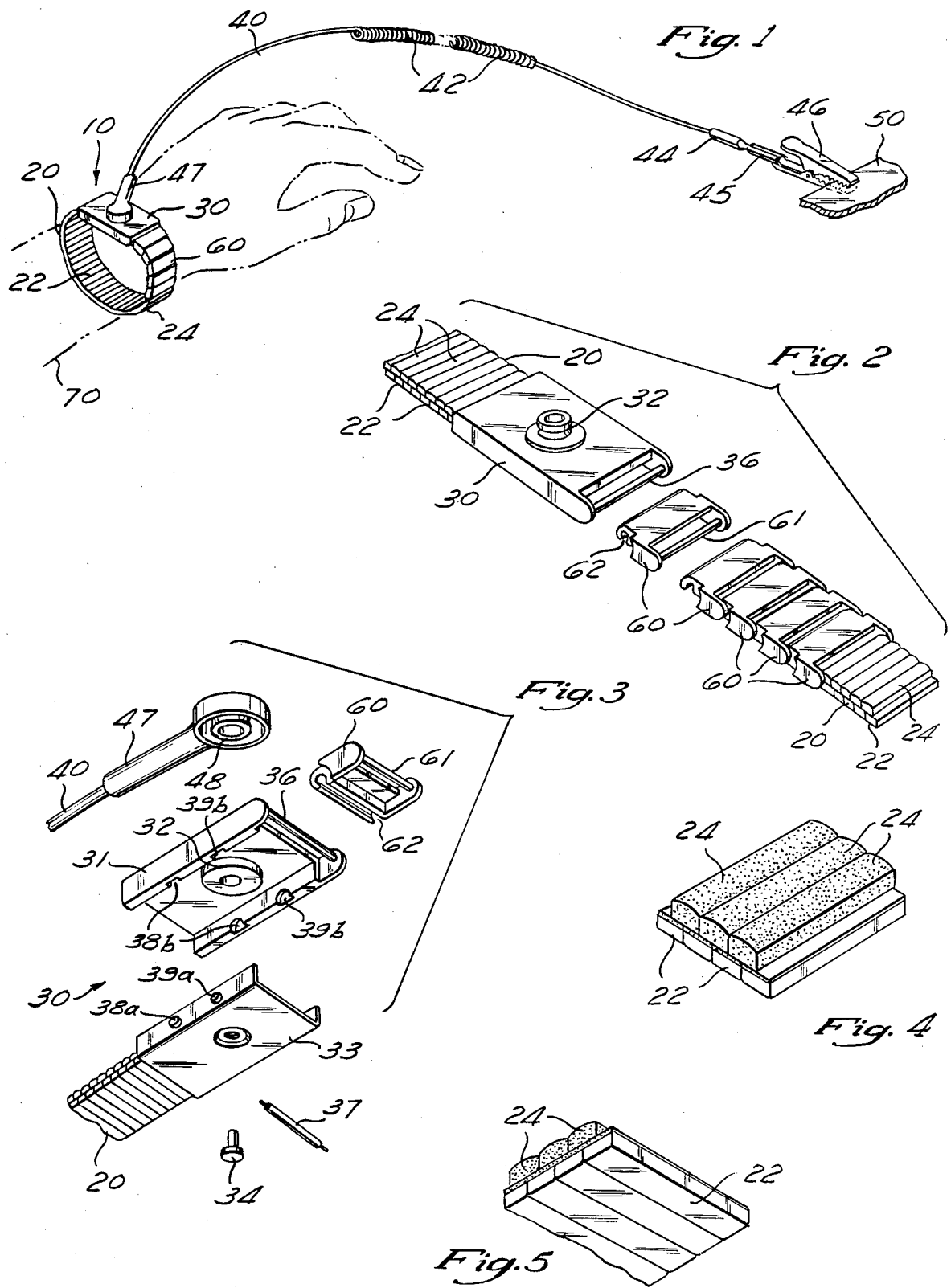

ELECTRICALLY CONDUCTIVE WRIST BRACELET WITH REMOVABLE CLASPING LINKS AND EXPANSION BAND

This application is a continuation of application Ser. No. 07/039,633 filed 4/17/87, now abandoned.

BACKGROUND OF THE INVENTION

1. Field of the Invention

The present invention generally pertains to electrically conductive bracelets worn on the leg or arm to drain or wick static electrical charge from the wearer. The present invention specifically concerns adjustable length expansion bracelets with an insulating surface upon the external circumference of the bracelet.

2. Description of the Relevant Art

As reported in U.S. Pat. No. 4,577,256, static electricity provides problems in the electronics and other industries, particularly with the advent of integrated circuits and other microelectronic components. Components such as integrated circuits, for instance, may be disabled or destroyed by over-voltage or power density resulting from static electricity. Certain junctions in such circuits can be destroyed by as little as a 50-volt potential, which radically changes the doping structure in their lattices. Power densities resulting from excessive potential and imperfections in a silicon circuit layout or structure can vaporize or radically alter the silicon substrate and thus impair or destroy a circuit's performance. Yet a person walking on a carpet on a dry day can accumulate as much as 30,000 volts of potential, and he can triboelectrically generate thousands of volts by simply changing his position in his chair or handling a styrofoam cup.

Such a person can inadvertently discharge such static electric potential into a circuit or component by touching it and causing overvoltage or excessive power density. Additionally, the potential in such a person's body can induce a charge in a circuit that can later cause overvoltage or excessive power density when the circuit is subsequently grounded. More and more frequently, therefore, personnel in industries in which integrated circuits and other microelectronic components are handled or assembled are taking measures to limit the failure rate of those circuits and components by attempting to keep both them and their environment at a zero electrical potential. Such measures include providing workers and work stations with antistatic carpet, conductive or dissipative grounded desk top work surfaces; hot air ion generators which emit ions to neutralize static charges; and grounding straps to keep workers at zero potential. The term "conductive" herein, and according to its customary usage in the art, means an electrical resistance of between zero and $10^5$ ohms. Similarly, "dissipative" means a resistance of between $10^5$ and $10^9$ ohms, "anti-static" means a resistance of between $10^9$ and $10^{14}$ ohms, and "insulative" means a resistance of more than $10^{14}$ ohms.

A grounding strap must have several features in order to perform its grounding function effectively. First, it must ensure that the wearer's skin is electrically connected to ground. This connection is typically accomplished by a conductive surface on the inside of a strap contacting the skin. The conductive surface is electrically connected to a grounding cord which leads from the strap to a grounded electrical connection. If the electrical contacting means on the inside of the strap becomes dirty or fouled by oil, perspiration or hair, then the strap may lose its effectiveness. It is therefore important to use a conductive material on the inner surface of the strap that does not easily become dirty or fouled.

Second, user comfort is a premier consideration because if the strap is uncomfortable, then the wearer will be tempted to remove it and can thereby cause damage to electrical components on which he is working. A strap that is easily stretchable, that is attractive and that poses minimum inconvenience to the wearer is therefore highly desired.

The situations in which grounding wrist straps are used heightens the importance of their being comfortable so that they are continuously worn and maintain continuous electrical contact with the skin. A person working on microelectronic components or integrated circuits may be completely unaware that he has accumulated minor static electrical discharges, and may therefore unknowingly be in a position to disable circuits on which he is working or which he is handling. If his strap is loose or he has removed it, he may be unaware that electrical discharges transmitted from his fingers are disabling these circuits. (A typical person cannot sense a static electrical discharge of less than approximately 3,500 volts.) No one may discover that the circuits have been disabled or damaged until hours, days or weeks later, when the circuits have been placed in components or devices which fail in the field. Removal and repair or replacement of these circuits once in the field is far costlier than avoiding potential failure while the wearer is handling the circuits. Thus, the wearer's employer typically must depend upon the effectiveness of the wrist strap to maintain a lower failure rate of such electronic circuits and components, by maintaining continuous electrical contact with the wearer's wrist and by providing him minimum temptation to remove the strap from his wrist.

These considerations have been addressed by several types of grounding straps. U.S. Pat. No. 4,373,175 issued Feb. 8, 1983 to Mykkanen ("Mykkanen"), for instance, discloses an extensible metal band similar to a Speidel watch band on which a snap fastener for a grounding cord is attached. Such a strap can be reasonably comfortable. However, its conductive metal outer surface can prove dangerous to the wearer if it contacts an electrical potential sufficient to electrocute the wearer.

U.S. Pat. No. 4,402,560 issued Sep. 6, 1983 to Swainbank ("Swainbank") discloses an expansive metal conductive wrist strap improved for having a resistor, enclosed within a housing, in the ground lead proximate the point of plugged electrical connection to the wrist strap. The housing is adapted to be grasped by the finders for plugging and unplugging the ground lead from the wrist strap.

Another type of prior art wrist strap is one wherein an all textile strap is impregnated with thermosetting conductive coating and fastened about the wrist of an operator. In all instances the wrist strap is connected by way of a swivel type snap connector and insulated conductor to a suitable device for making a connection to ground at the work station.

One fabric grounding strap reportedly improved for comfort is disclosed in U.S. Pat. No. 3,857,397 issued Dec. 31, 1974 to Brosseau ("Brosseau"). Outer and inner conductive polyolefin layers sandwich an intermediate nylon scrim layer to form the band. Hook and loop (Velcro) fastening materials can accumulate on such surfaces and interfere with electrical contact between the band and the skin. Further, carbon particles tend to wear off onto the wrist, causing black stripes on the wrist. The nonstretchable nature of such bands means that the wearer must adjust then to be tight enough to cause sufficient elecrical contact, but loose enough to be comfortable, and skin contact can be lost or intermittent.

Another approach to many of these problems is disclosed in U.S. Pat. No. 4,398,277 issued Aug. 9, 1983 to Christiansen and Westberg ("Christiansen"). This strap is made of knitted stretchable fabric containing stainless steel fibers. A plastic and metal fitting permanently closes the strap into a loop of predetermined size and has a connection for a grounding cord. This strap can prove uncomfortable to the wearer, however, unless his wrist comports with the predetermined strap size offered by the manufacturer. Further, the knitted fabric permits the strap to roll over on itself as it is being pulled over the hand and causes the strap to become thinner as it is stretched. Because the fabric is knitted, it can also "pull" and "run" when snagged. Perhaps more important it has been discovered that the electrical conductivity of the Christiansen strap decreases as the strap is relaxed, and thus varies from one stretched state to another. This phenomenon probably occurs because the metallic strands in the conductive yarns are pulled more tightly together in the knitted materials, wherein they are stretched and are separated from one another to a certain extent in the knitted conductive yarns as the strap is relaxed.

A reported solution to some of these problems with grounding wristbands of fabric is discussed in U.S. Pat. No. 4,577,256 issued Mar. 18, 1986 to Breidegam ("Breidegam"). A woven stretchable grounding strap is shown which uses conductive fibers on the inside surface of the strap to contact the skin and to conduct electrical charges to a grounding cord attached to the strap. Face yarns exposed on the outer surface are woven to form designs. The woven fabric material of the strap is attached to a clasp allowing the strap to be adjustable in size. Becasue of the woven nature of the fabric material and the adjustable clasp, the strap is reported to be more comfortable than other conductive eleastic wrist straps. The woven fabric material is also reported to be advantageous because it stretches easily, it is inexpensive, and it does not roll over onto itself as it is being drawn over the hand. This woven stretchable grounding strap is in widespread industrial usage circa 1987.

It is desirable to create an adjustable, inexpensive, and effective grounding wristband, or bracelet, substantially out of metal and/or plastic which maintains all the advantages of prior art conductive wristbands of both the metal expansion band and fabric type while offering improved durability, sanitation, and expandability. The diverse watchband art should be compared. Fabric and leather watchbands are well-known, and popular. But metal, plastic, and metal/plastic watchbands are also popular. The prior art conductive metal wrist straps have superimposed the electrical requirements for a conductive, plugable ground lead, wrist strap onto standard form metal link expansion bracelets. This adaption does not account for establishing (i) maximum size range, (ii) maximum ease of size adjustment, (iii) maximum comfort, and (iv) minimum cost in a metal wrist strap to be used by both sexes in a production environment.

SUMMARY OF THE INVENTION

The present invention is embodied in an electrically conductive wrist bracelet, particularly made of metal and plastic, which connects via a plugable grounding cord to electrical ground for draining static electrical charge from the wearer of such wrist bracelet. The bracelet includes a spring-biased expansion band made from a multiplicity of metal bar members. This band attaches at one end, nominally by a spring-loaded watchband pin, to a clasp member. The clasp member, nominally having a metal base and a plastic shell, or housing, also mounts an electrical plug jack to which a swivel connection is made by a coiled grounding cord which further connects to ground.

Further in the preferred embodiment bracelet in accordance with the present invention, the expansion band permanently attaches at its other end to a plurality of links, nominally formed of plastic. Each one of a plurality of such links presents a pivot bar on one end and a clasp aperture or slot which is formed in a complementary configuration to snap over a pivot bar of an adjacent link and pivotably retain the same. A linear array of these seperately removable and replaceable plastic links, nominally five in number, are snapped together one to the next between the band and clasp member in order to complete the circumference of the bracelet.

In use, preliminary lengthening or shortening of the bracelet may be readily obtained by user insertion or removal of one or more of the plastic links. Regardless of the number of links used, the bracelet may be readily manually clasped and unclasped between the end one of the plurality of links connected as an array and the clasp member in which it engages, and/or between any adjacent ones of the plurality of links. Another adjustment in the length in the bracelet is obtained at the time of manufacture by varying the number of spring-biased bar members, nominally 92, which are within the expansion band. The size-adjusted bracelet may readily be placed onto the wrist either by slipping the hand into the closed bracelet through extending the expansion band or, if preferred, by opening and then reclosing the bracelet by respectively unsnapping and resnapping any one or ones of the plastic links.

The metal expansion band and metal/plastic clasp member are electrically conductive at the bracelet's interior circumference, but are electrically insulating at the bracelet's exterior circumference. Particularly, the exterior circumference of the expansion band may be painted and the exterior shell of the clasp may be formed of plastic. The grounding cord, which makes a swivel plugjack electrical connection at the clasp member, electrically connects through the shell of the clasp member to the electrically conductive metal base of the clasp member at the interior circumference of the bracelet.

The exterior surface of the bracelet may be colored coded and/or legended with information or identification in any of its parts including the clasp member, the expansion band of bar members, and/or the array of links. The bracelet is durable, sanitary, readily cleaned, and inexpensive. The bracelet is generally heavier than fabric wristband, and presents an appropriate heft to maneuver the ground lead to which it is plugably affixed. The metal and plastic components feel generally cooler to the flesh than do fabric wristbands, and impart the normal weight and feel of a metal expansion watchband and an accompanying metal watch.

BRIEF DESCRIPTION OF THE DRAWINGS

These as well as other features of the present invention will become more apparent upon reference to the drawings wherein:

FIG. 1 is a perspective view showing a grounding system incorporating the preferred embodiment electrically conductive wrist bracelet in accordance with the present invention.

FIG. 2 is an exploded perspective view showing the clasp member, the pluraliy of links, and a portion of the expansion band, which are all part of the preferred embodiment wrist bracelet in accordance with the present invention.

FIG. 3 is a second exploded perspective view particularly showing the detailed construction of the clasp member and of the links, both part of the preferred embodiment wrist bracelet in accordance with the present invention.

FIG. 4 is a detailed perspective view showing the top surface of the expansion band, part of the preferred embodiment wrist bracelet in accordance with the present invention.

FIG. 5 is a detailed perspective view showing a bottom surface of the expansion band, part of the preferred embodiment wrist bracelet in accordance with the present invention.

DESCRIPTION OF THE PREFERRED EMBODIMENT

As an overview, the present invention is embodied in an electrically conductive wrist bracelet which includes both removable and replaceable links, a clasp member electrically connectable by a grounding cord to ground, and an expansion band. The circumference of the bracelet may be adjusted upon its initial fabrication by a varying the number of spring-biased members within the expansion band, and may be further increased or decreased by the user at the time of use by a respective insertion, or deletion, of one or more of the links. The bracelet is expandable by a distension of the expansion band. The bracelet may be readily unclasped at the point of attachment of the end link to the clasp member, or between any successive ones of the links themselves.

A perspective view of a preferred embodiment electrically conductive wrist bracelet in accordance with the present invention, particularly for in use within an electrical grounding system, is shown in FIG. 1. The bracelet 10 is normally affixed around the wrist 70, but may be affixed around the ankle or at other locations upon the human appendages. The bracelet 10 includes an expansion band 20 consisting of a multiplicity of spring-biased bar members or elements 22, 24 arrayed as an expansible linkage. There are nominally 46 each of interior bar members 22 and exterior bar members 24, which are nominally formed of metal and interconnected in a conventional manner with metal springs. The expansion band 20 is equivalent to expansion watchbands, such as those manufactured by the Speidel Corporation under the trade name "Twist-O-Flex".

The expansion band 20 is connected at one end to a clasp member 30. The clasp member 30 pluggably receives and electrically connects to the grounding cord 40, which preferably contains a one megaohmn resister (not shown) for preventing electric shock to the user if such grounding cord 40 were to accidentally contact a power source. The grounding cord 40 is normally connected to a ground 50, thereby draining, or wicking, body electrical static charges from the wearer's wrist to electrical ground. The grounding cord 40 further nominally includes loop coils 42 which allow for convenient expansion and contraction in the length of the grounding cord. The end of grounding cord 40 opposite to clasp member 30 includes electrical plug jack connectors 44, 45 which are nominally of the banana plug type. The end of ground cord 40 terminates in an electrical clip connector 46, nominally of the alligator type, for convenient electrical connection to ground plane 50. Finally in FIG. 1, the bracelet 10 is completed by a plurality of selectively separately removable and replaceable links 60.

An expanded perspective view of the preferred embodiment electically conductive wrist bracelet in accordance with the present invention is shown in FIG. 2. The expansion band 20 is made up of a multiplicity of exterior spring-biased bar members 24, which collectively provide an outer circumferential surface to the expansion band 20, and also of a multiplicity of interior spring-biased bar members 22 which likewise provide an inner cirucumferential surface to the expansion band 20. The expansion band 20 is connected at one end to clasp member 30 in a manner which will be shown in expanded detail in FIG. 3, and at the other end to a first end one of links 60.

Each of the links 60 (of which a nominal five are illustrated) is individually selectively seperately removable and replaceable within the wrist bracelet 10. Each link 60 presents a pivot bar 61 on one end, and a pivot aperture or clasp slot 62 on the other end sized to releasably pivotably snap onto and retain, or clasp, a pivot bar 61 of an adjacent one of the plurality of links 60. The pivot bar 61 of the individual one end link 60 which connects to an individual end one of the spring-biased bar members 22, 24 of the expansion band 20, nominally to an exterior spring-biased bar member 24, is preferably permanently grasped by this end one spring-biased bar member. Particularly, an individual end one spring-biased bar member 22, 24 has an aperture (not shown) which might normally slip a watchband pin 37 (shown in FIG. 3). In the bracelet 10 this aperture within the individual end one exterior spring-biased bar member 24 is permanently affixed about the pivot bar 61 of an individual first end one of the links 60. Similarily, the clasp member 30 presents at one end its own pivot rod 36. This pivot rod 36 is received into the pivot aperture 62 of a second end one of the arrayed and clasped links 60.

Considering the clasping connection achieved in and by the bracelet 10 which is shown in expanded partial view in FIG. 2, it may be noted that the bracelet 10 may be manually clasped and unclasped between the second end one of the arrayed and clasped links 60 and the clasp member 30. Likewise, the bracelet may equally as well be manually clasped and unclasped between adjacent one or ones of the links 60 themselves. The links 60, which are normally formed of molded plastics, are inexpensive and therefore disposable. As such, plural links may be supplied with the wristband at the time of manufacture and, at a later time of use, may be removed or replaced by the user to adjust the length of the wristband with extra links being discarded. The links are normally stocked in a large number of solid colors in support of a manufacturing operation employing many electrically conductive wrist bracelets in accordance with the present invention. The links 60 may bear leg-ends, personel identification, stick-on watchband-type calenders, or innumerable like features upon their surfaces. In some cases a modified link 60 (modified) may be employed which presents two pivot apertures 62 and no pivot bar 61. Such a female-female clasping link 60 (modified) permits the inclusion of the user's own watch within bracelet 10 in substitution for that portion of the circumferential extent of the bracelet 10 which is normally occupied by several of the links 60. The colors, and color codings of the plurality of links 60 permit personalized identification, and customization to personal esthetics of bracelet 10.

An exploded perspective view of the detailed construction of clasp member 30 and links 60 is shown in FIG. 3. The clasp 30 mounts, in an approximately central position upon its top surface (which is disposed toward the outer circumference of bracelet 10) an electrical connector 32, nominally a plugable free-swivel snap connector. This snap-on swivel electrical connector 32 mates with a complementary electrical connector 48 encased within plastic strain relief 47 at the end of the grounding core 40. Normally the male portion of the snap-on electrical connector is mounted to the clasp member 30 as connector 32, and the female portion is mounted to at the end of the grounding cord 40 as connector 48—although this can be reversed.

Continuing in FIG. 3, the clasp member 30 includes an upper member 31 nominally made of molded plastic, and a lower member 38 nominally made of metal. The two members are affixed to each other, additionally securing the electrical connector 32, by a fastener, nominally a metal rivet 34, which attaches both members. Between the upper member 31 and the lower member 33, the expansion band 20 is affixed to lower member 33 and (and thus also to upper member 31) either at the first set of registry holes 38a, or at the second set of registry holes 39a, by spring-loaded watchband pin 37. The spring-loaded watchband pin 37 slips a complementary cavity (not shown) formed upon an end one of spring-biased members 22, 24 at the end of the watchband 20, and projects into one of the opposed registry hole sets 38a or 39a. The projections resultant from the stamping of registry hole sets 38a, 39a, and which extend beyond each side of lower member 33 are accomodated in a respective first set of relieved areas 38b, or the second set of relieved areas 39b, within upper member 31.

The lower member 33 to clasp member 30 is made symmetrical with two registry hole sets 38a, 39a for ease of manufacturing assembly. The watchband pin 37 will project into that set of registry holes, in order to connect watchband 20, which are at that end of lower member 33 which is opposite to that end which will be proximate to pivot rod 36 in the completed assembly of clasp member 30. In FIG. 3 this means that watchband pin 37 will project into registry hole set 38a. The watchband pin 37 will also always project into relieved areas 38b.

The electrical path within the bracelet 10, and particularly within the expansion band 20 component thereof, will be further discussed with reference to FIGS. 4 and 5. The expansion band 20, shown in expanded top perspective view in FIG. 4 and corresponding bottom perspective view in FIG. 5, has exterior (to bracelet 10) spring-biased bar members 24 and interior spring-biased bar members 22 which are mechanically equivalent. However, these members 22, 24 are not electrically identical. Mainly, the exterior spring-biased bar members 24 are formed to be electrically insulating whereas the interior spring-biased bar members 22 are formed to be electrically conductive. This dichotomy in the bar members 22, 24 between electrically insulating and electrically conductive may be obtained simply by painting the expansion band 20 of an assembled bracelet 10 upon the top surfaces of the exterior spring-biased bar members 24. The precision of such painting, nominally with a high strength epoxy enamel, is not critical. The painting may overlap onto the edges of spring-biased exterior bar members 24. The purpose of the painting is simply to generally make the outer circumference of the wrist bracelet 20 to be generally electrically insulating. When the outer circumference of wrist bracelet 20 is electrically insulating then neither it nor the plastic links 20 nor the shell 31 of plastic clasping member 30 (other than connector 32 through the shell 31) will channel electrical current to the user wearer of the bracelet 10 even should the exterior surface of such bracelet inadvertently contact a source of electrical energy.

The links 60 are normally entirely formed of plastic, and are entirely electrically insulating. If such links are, as is possible, alternatively formed of metal, then the exterior surfaces of such links are also preferably painted so to form an insulating barrier. The upper body member, or shell, 31 of the clasp member 30 is plastic save for the electrical connector 32. The electrical connector 32 is normally completely covered and surrounded by the electrical attachment of grounding cord 40. The bracelet 10 is thus electrically insulating on its entire exterior circumference while being electrically conductive in at least part of its interior circumference.

In operational use, the electrically conductive interior circumference of expansion band 20 is formed from the unpainted metal surfaces of interior spring-biased members 22 and the lower body member 33 of clasp member 30. Both these components electrically contact the body appendage of the user, nominally the user's wrist 70. An electrical path is thereby enabled from these conductive metal members through rivet 34 through electrical connector 32 (both part of clasp member 30) through electrical connector 48 and hence via grounding cord 40 to ground 50. This electrical path serves to drain, or wick, static electrical charge to ground which might elsewise accumulate upon the body of the user.

The electrically conductive wrist bracelet 10 in accordance with the present invention may be readily positioned over the hand and onto its preferred operative position upon wrist 70 merely by expansion of band 20. Alternatively, the bracelet 10 may be clasped and unclasped at the position of any of links 60. In use, the bracelet 10 feels substantially similar to a metal expansion watchband, and exhibits a generally similar weight, tension, and feel. This type of wrist bracelet is preferred by some users, particularly for evidencing characteristics which are close to those with which the user may be familiar with from wearing a standard metal expansion watchband.

In accordance with the preceding explanation, the present invention will be seen to incorporate diverse features, and to readily be incorporated within diverse embodiments. Consequently, the present invention should be defined by the language of the following claims, only, and not solely in accordance with that particular preferred embodiment within which the invention has been taught.

I claim:

1. An electrically conductive bracelet comprising:
an electrically conductive clasp member electrically connectable to a ground;
a first plurality of spring-biased bar members which are arrayed as an expansible band which is connected at one end to the clasp member; and
a plurality of selectively separately removable and replaceable links positioned between the clasp member and the expansible band, each said removable and replaceable link comprising a link body having opposing lateral ends with a pivot bar extending transversely across one end thereof and a hook-like flange forming a clasp slot extending transversely across the other end thereof;
each said clasp slot being sized and configured to be directly positionable over the pivot bar of an adjacent one of said links and directly and non-compressively advanceable there onto such that the said pivot bar will snap into and be frictionally retained within said clasp slot; and
wherein the clasp member, the expansible band, and the array of removable and replaceable links collectively form a bracelet which is electrically conductive in at least the clasp member.

2. The bracelet according to claim 1 wherein the bar members are electrically conductive and are arrayed as an electrically continuous expansible band which is electrically as well as physically connected to the clasp member; wherein the bracelet is electrically conductive in at least the clasp member and the expansible band.

3. The bracelet according to claim 1 wherein the bracelet may be manually clasped and unclasped between an end one of said removable and replaceable links connected as an array to the clasp member and also between adjacent ones of the plurality of links.

4. The bracelet according to claim 1 wherein each one of said removable and replaceable links has an upper surface, a lower surface, opposing longitudinal ends, and opposing transverse edges, and comprises:
a pivot bar extending transversely at one longitudinal end of said link, said pivot bar being directly engageable from said upper surface of said link, and
a hook-shaped flange having a slot aperture formed therewithin, said flange extending from the longitudinal end of said link which is opposite said pivot bar, said slot aperture being sized and configured to be directly and non-compressively snap fit upon the pivot bar of an adjacent one of said removable and replaceable links.

5. The bracelet according to claim 1 wherein the clasp member comprises:
a clasp member body presenting a set of opposed registry holes along the length of its body; and
a spring-loaded watchband pin engaging a bar member and the registry holes.

6. The bracelet according to claim 5 wherein the clasp member body comprises:
an electrically conductive base positioned toward the interior of the bracelet;
an electrically insulating shell positioned toward the exterior of the bracelet;
an electrical connector within the shell which is connectable to ground; and
electrical path means for making electrical connection between the electrically conductive base and the electrical connector.

7. The bracelet according to claim 1 wherein the addition to or the deletion from the bracelet of each of the plurality of links gives a like plurality of intermediate adjustments respectively, increasing or decreasing the length of the bracelet.

8. The bracelet according to claim 1 wherein the first plurality of spring-biased bar members arrayed as an expansible band present an electrically conductive surface to the interior of the bracelet and present an electrically insulating surface to the exterior of the bracelet.

9. The bracelet according to claim 8 wherein the conductive surface is metal and wherein the insulating surface is painted metal.

10. The bracelet according to claim 3 wherein each one of the plurality of links may be added to or deleted from the bracelet in order to respectively lengthen or shorten its length.

11. The bracelet according to claim 4 wherein each of the plurality of links comprises:
plastic material exhibiting resiliency in order that the pivot aperture retains and releases the pivot bar respectively during the clasping and unclasping respectively by a snap-lock clasping action and a snap-unlock unclasping action.

12. A method of assembling an electrically conductive bracelet sized to fit about the wrist, the assembly method comprising:
first connecting a first end of an electrically conductive expansion band by pinning with a watchband pin to a first end of an electrically conductive clasp member including a means for attaching said clasp member to an electrical ground, wherein connection is made between the band and the electrically ground clasp member;
second connecting a second end of the band to a first one of a plurality of removable and replaceable links by affixing a pivot bar presented on one end of the first link within a pivot bar engaging means presented by the second end of the band;
third manually snap connecting the plurality of removable and replaceable links one to the next by serially non-compressively snap fitting the pivot bar present on one end of one link within the slot aperture present on the opposing end of an adjacent link; and
fourth connecting an end one of said removable and replaceable links to a second end of the clasp member by snap fitting a pivot bar present on said clasp member within a slot aperture present on said first link;
wherein the total circumference of the connected clasp member, the expansion band, and the plurality of links connected in a closed loop is appropriately sized to fit about the wrist.

13. The assembly method according to claim 12 wherein the first connecting is by a watchband pin which slips an aperture within the first end of the expansion band and which extends, under spring force, at both pin ends into corresponding opposed holes within a first end of the clasp member, therein retaining by pinning with a watchband pin.

14. The assembly method according to claim 13 wherein the expansion band first end aperture is functionally equivalent in the pinning as the expansion band second end aperture is in the affixing.

15. The assembly method according to claim 12 wherein the third connecting is of links having and presenting at one end a pivot bar aperture which is complementary to the pivot bar and is by forceably snapping each pivot bar into the pivot bar aperture of an adjacent length, therein clasping the links one to the next.

16. The assembly method according to claim 15 wherein the fourth connecting is of the second end of the member which has and presents a pivot rod which is complementary to the pivot aperture of the end one of the clasped plurality of links, therein clasping the plurality of links to the member.

17. The assembly method according to claim 16 wherein all clasping by forceably snapping results in flexible and pivotable connections.

18. An adjustable wristband for draining static electricity from the body of a wearer, said wristband comprising the combination of:

an electrically conductive clasp member electrically connectable to a ground and having first and second longitudinal ends with a pivot rod extending transversely across said second longitudinal end;

an expansible band having a first longitudinal end and a second longitudinal end, said first longitudinal end of said expansible band being connected to the first longitudinal end of said clasp member; and a plurality of removable links interconnected in a linear array, each of said removable links having opposing longitudinal ends with a pivot bar extending transversely across one longitudinal end thereof and a hook-shaped flange formed on the other longitudinal end thereof, said hook-shaped flange defining a slot-like aperture sized and configured to be directly and non-compressively snap-fit over the pivot bar of another removable link and to pivotally retain the pivot rod of said clasp member and said pivot bar of each said removable link; and the pivot bar of a link located at one end of said linear array being connected to the second longitudinal end of said expansible band and the slot aperture of a link at the other end of said linear array being connectable to the pivot rod located on the second longitudinal end of said clasp member so as to form a continuous band encircling the wrist of the user.

* * * * *